(12) United States Patent
Jin et al.

(10) Patent No.: US 10,746,725 B2
(45) Date of Patent: Aug. 18, 2020

(54) METHOD AND DEVICE FOR DETECTING ENDOTOXIN

(71) Applicants: SHINSHU UNIVERSITY, Matsumoto-shi, Nagano (JP); KAIJO CORPORATION, Hamura-shi, Tokyo (JP); SHIBUYA CORPORATION, Kanazawa-shi, Ishikawa (JP)

(72) Inventors: Jiye Jin, Matsumoto (JP); Nobuyuki Kurashina, Hamura (JP); Junichiro Soejima, Hamura (JP); Toshiharu Sawada, Kanazawa (JP)

(73) Assignees: SHINSHU UNIVERSITY, Matsumoto-Shi, Nagano (JP); KAIJO CORPORATION, Hamura-Shi, Tokyo (JP); SHIBUYA CORPORATION, Kanazawa-Shi, Ishikawa (JP)

( * ) Notice: Subject to any disclaimer, the term of this patent is extended or adjusted under 35 U.S.C. 154(b) by 244 days.

(21) Appl. No.: 16/019,695

(22) Filed: Jun. 27, 2018

(65) Prior Publication Data

US 2019/0011430 A1    Jan. 10, 2019

(30) Foreign Application Priority Data

Jul. 6, 2017 (JP) .................. 2017-133011

(51) Int. Cl.
| | |
|---|---|
| *G01N 33/49* | (2006.01) |
| *G01N 33/579* | (2006.01) |
| *G01N 27/327* | (2006.01) |
| *A61M 1/34* | (2006.01) |

(Continued)

(52) U.S. Cl.
CPC ..... *G01N 33/4915* (2013.01); *G01N 27/3271* (2013.01); *G01N 27/3275* (2013.01); *G01N 33/492* (2013.01); *G01N 33/579* (2013.01); *A61M 1/3479* (2014.02); *B01D 61/243* (2013.01); *C02F 1/441* (2013.01); *G01N 2400/50* (2013.01)

(58) Field of Classification Search
CPC ............. G01N 33/4915; G01N 33/579; G01N 27/3271; G01N 27/3275; G01N 33/492; G01N 2400/50; G01N 27/26; A61M 1/3479; B01D 61/243; C02F 1/441
See application file for complete search history.

(56) References Cited

U.S. PATENT DOCUMENTS 8,211,651 B2 * 7/2012 Yabusaki ................. C12Q 1/37
435/7.1

FOREIGN PATENT DOCUMENTS

| JP | 2016-151482 A | 8/2016 |
| WO | WO 2013/180176 A1 | 12/2013 |

* cited by examiner

*Primary Examiner* — Jennifer Wecker
*Assistant Examiner* — Michael Paul Shimek
(74) *Attorney, Agent, or Firm* — Flynn Thiel, P.C.

(57) ABSTRACT

Endotoxin is detected by electrochemical measurement. A detection device 15 of endotoxin detects endotoxin contained in a fluid to be tested (for example, a dialysate) specifically in the following manner. First, the fluid to be tested is brought into contact with an adsorbent 17 that adsorbs endotoxin to cause the adsorbent 17 to adsorb the endotoxin. Then, a basic solution is brought into contact with the adsorbent 17 to desorb the endotoxin. Electrochemical measurement of the basic solution containing the desorbed endotoxin is performed. The endotoxin can be detected by the electrochemical measurement with high sensitivity at low cost.

3 Claims, 3 Drawing Sheets

(51) Int. Cl.
*B01D 61/24* (2006.01)
*C02F 1/44* (2006.01)

METHOD AND DEVICE FOR DETECTING ENDOTOXIN

BACKGROUND OF THE INVENTION

Field of the Invention

The present invention relates to a method and a device for detecting endotoxin, and more particularly to a method and a device for detecting endotoxin by electrochemical measurement.

Description of the Related Art

In a hemodialyzer that performs online hemodiafiltration or hemofiltration using a dialysate, endotoxin must not be brought into blood through the dialysate, and for that purpose, it is required that a filter for trapping endotoxin is provided in a dialysate circuit to clean the dialysate.

Endotoxin is a general term for toxic substances that form outer membrane of gram-negative bacteria such as colibacillus or *Salmonella*, of which entity is Lipopolysaccharide (LPS) generally consisting of a polysaccharide portion and a lipid portion called Lipid A. Since endotoxin present in blood even in an extremely small amount may cause pyretic action, death from shock, intravascular coagulation, or sepsis, contamination of drugs and medical devices with endotoxin is a critical control matter.

As a method for detecting such endotoxin, a Limulus test using a reagent derived from a blood cell extract of horseshoe crab is generally known, and this test can detect endotoxin with extremely high sensitivity. However, the reagent used is expensive, and if endotoxin contained in a dialysate is to be detected, the dialysate needs to be diluted by 1000 times so that a component of the dialysate does not affect detection. Thus, the test cannot be easily performed in an installation environment of a hemodialyzer.

In this respect, Japanese Patent Laid-Open No. 2016-151482 proposes a method for electrochemically measuring a concentration of endotoxin.

SUMMARY OF THE INVENTION

As described above, the endotoxin consists of a polysaccharide portion and a lipid portion. For saccharides, monosaccharide and oligosaccharide (disaccharide) can be electrochemically measured, but polysaccharide generally has low electrochemical activity. The lipid portion does not exhibit electrochemical activity, and preferentially adsorbs on an electrode surface which will decrease in sensitivity of measurement.

For such electrochemical measurement of endotoxin, in the method of Japanese Patent Laid-Open No. 2016-151482, endotoxin is first trapped by a carrier, and then an endotoxin recognition probe having a heavy metal compound region is reacted with the carrier and trapped by the endotoxin. Thus, an endotoxin recognition molecular probe is trapped according to an amount of endotoxin trapped by the carrier. At this time, an acid solution is added to the carrier having trapped the probe to elute heavy metal as heavy metal ions from the probe, an eluate containing the heavy metal ions is added to a predetermined buffer, and a concentration of heavy metal ions in the eluate is determined using a working electrode capable of electrochemical measurement of heavy metal ions.

With such a method of Japanese Patent Laid-Open No. 2016-151482, a concentration of endotoxin can be electrochemically measured. However, the endotoxin recognition probe having the heavy metal compound region trapped by the endotoxin needs to be prepared, and it is difficult to easily perform a test. Also, the measurement is indirectly performed through heavy metal in the endotoxin recognition probe, and the endotoxin is not directly detected, which may cause measurement errors.

An object of the present invention is to provide a method and a device for detecting endotoxin capable of detecting endotoxin by electrochemical measurement with high sensitivity at low cost.

In view of the above described circumstances, the present invention according to claim 1 provides a method for detecting endotoxin by electrochemical measurement, including the steps of: bringing a fluid to be tested into contact with an adsorbent that adsorbs endotoxin to adsorb the endotoxin; bringing a basic solution into contact with the adsorbent having adsorbed the endotoxin to desorb the endotoxin from the adsorbent; and electrochemically measuring the basic solution containing the desorbed endotoxin.

Also, the present invention according to claim 3 provides a device for detecting endotoxin by electrochemical measurement including: an adsorbent that adsorbs endotoxin; supply means for supplying a basic solution for desorbing the endotoxin; and measurement means for performing electrochemical measurement, wherein a fluid to be tested is brought into contact with the adsorbent to adsorb the endotoxin, then the basic solution is brought into contact with the adsorbent to desorb the endotoxin, and the basic solution containing the desorbed endotoxin is electrochemically measured.

With such a configuration, endotoxin can be detected by electrochemical measurement with high sensitivity at low cost.

DETAILED DESCRIPTION OF THE PREFERRED EMBODIMENTS

Figure 1:
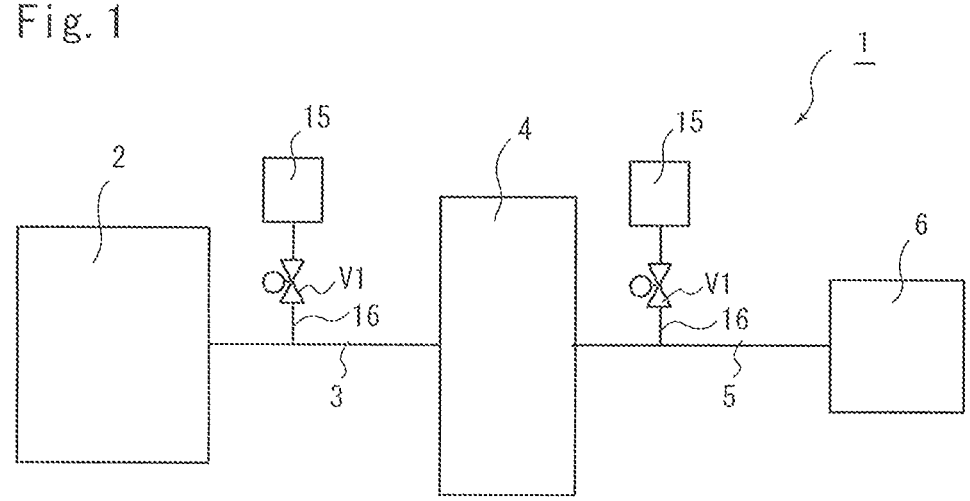
FIG. 1 is a configuration diagram of a dialysis system including a device for detecting endotoxin according to the present invention.

The present invention will be described in connection with a shown embodiment. FIG. 1 shows a dialysis system 1 in which reverse osmosis water supplied from a reverse osmosis water supply device 2 is fed through a pipe 3 to a dialysate supply device 4, and a dialysate prepared by the dialysate supply device 4 is supplied through a pipe 5 to a hemodialyzer 6.

Figure 2:
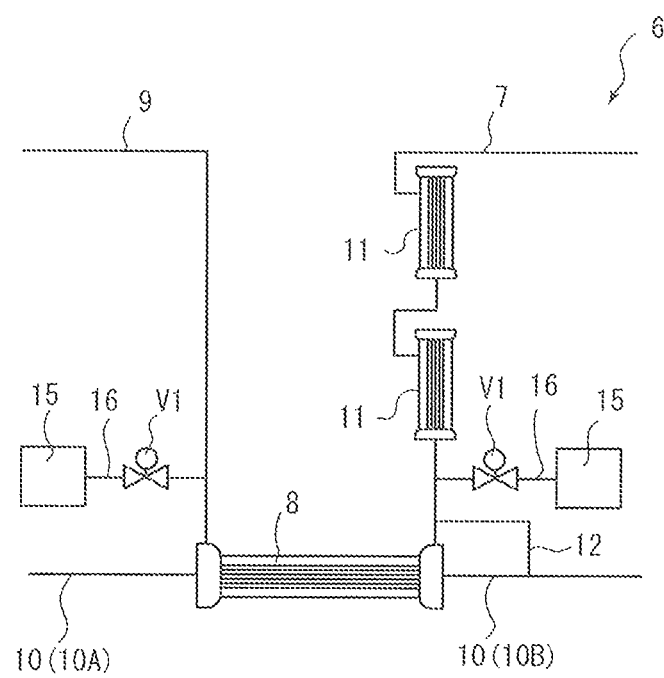
FIG. 2 is a configuration diagram of a hemodialyzer including the device for detecting endotoxin according to the present invention.

FIG. 2 shows a part of a configuration of the hemodialyzer 6 in which the dialysate supplied through the pipe 5 is supplied through a supply passage 7 to a dialyzer 8, and discharged from the dialyzer 8 to a discharge passage 9. A blood circuit 10 is connected to the dialyzer 8, and blood withdrawn from human body is fed from an artery passage 10A to the dialyzer 8, in which a waste product or extra water is removed from the blood, which is then returned from a vein passage 10B to the human body.

The supply passage 7 includes two trap filters 11 that trap endotoxin in the dialysate. Between the second trap filter 11 and the dialyzer 8, a replacement fluid passage 12 connecting the supply passage 7 and the blood circuit 10 is connected. The replacement fluid passage 12 can supply the dialysate from the supply passage 7 to the blood circuit 10.

In FIGS. 1 and 2, reference numeral 15 denotes a detection device of endotoxin according to the present invention, which is configured to draw a fluid to be tested into the detection device 15 through a drawing passage 16 including an on-off valve V1.

In the dialysis system 1 in FIG. 1, the drawing passage 16 is connected to the pipe 3 that feeds reverse osmosis water from the reverse osmosis water supply device 2 to the dialysate supply device 4, the reverse osmosis water is extracted as a fluid to be tested and subjected to a test, and also the drawing passage 16 is connected to the pipe 5 that feeds the dialysate from the dialysate supply device 4 to the hemodialyzer 6, and the dialysate is extracted as a fluid to be tested and subjected to a test.

Further, in the hemodialyzer 6 in FIG. 2, the drawing passage 16 is connected to the supply passage 7 between the second trap filter 11 and the dialyzer 8, and the cleaned dialysate having passed through the trap filters 11 is extracted as a fluid to be tested and subjected to a test. Also, the drawing passage 16 is connected to the discharge passage 9 connected to the dialyzer 8, and the used dialysate having passed through the dialyzer 8 is extracted as a fluid to be tested and subjected to a test.

Figure 3:
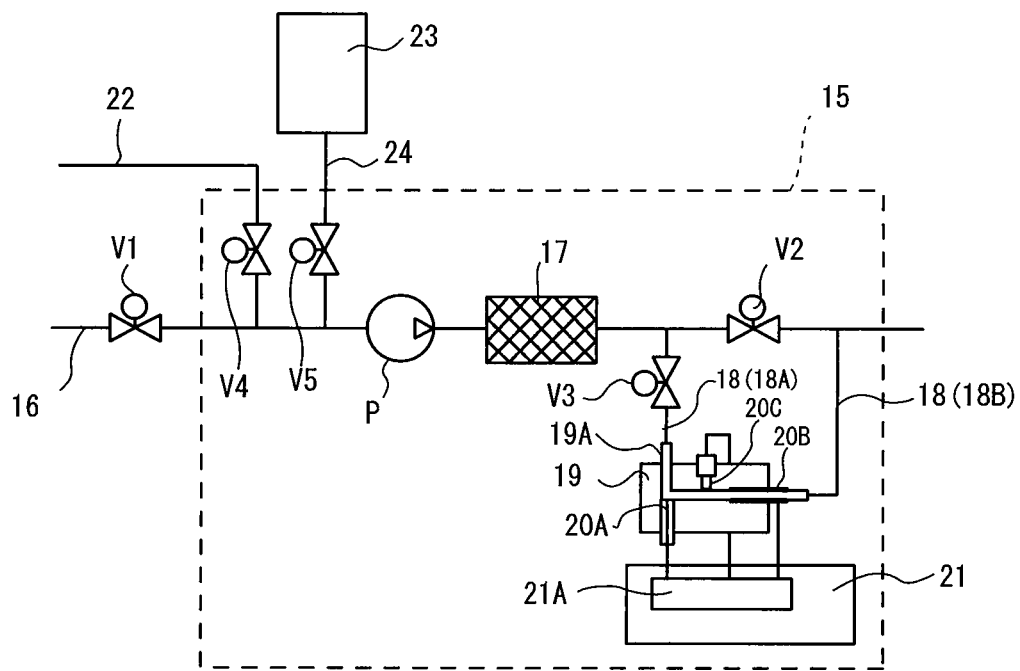
FIG. 3 is a configuration diagram of the device for detecting endotoxin according to the present invention.

FIG. 3 shows an internal configuration of the detection device 15. In the drawing passage 16 through which the fluid to be tested is drawn, a pump P for drawing the fluid to be tested to a downstream side of the on-off valve V1 is provided, an adsorbent 17 that fills a cylindrical column and selectively adsorbs endotoxin is provided on a downstream side of the pump P, and an on-off valve V2 is further provided on a downstream side of the adsorbent 17. An inflow passage 18A in a measurement circuit 18 is connected between the adsorbent 17 and the on-off valve V2, and an outflow passage 18B is connected to a downstream side of the on-off valve V2. An on-off valve V3 is provided in the inflow passage 18A, and a measurement cell 19 that performs electrochemical measurement by a three-electrode method is provided between the inflow passage 18A and the outflow passage 18B. The adsorbent 17 that selectively adsorbs endotoxin is known, for example, from International Publication No. WO2013180176 or the like.

A flow path 19A is formed in the measurement cell 19, and a working electrode 20A, a counter electrode 20B, and a reference electrode 20C are provided to face the flow path 19A. The electrodes 20A, 20B, 20C are connected to a potentiostat 21A provided in a control unit 21, and constitute measurement means for performing the electrochemical measurement. For the electrodes provided in the measurement cell 19, generally, the working electrode 20A is made of gold, the counter electrode 20B is made of platinum, and the reference electrode 20C is made of silver/silver chloride. In this embodiment, however, the working electrode 20A is formed of a carbon core modified with gold nanoparticles, and the reference electrode 20C is formed of a stainless tube.

The potentiostat 21A serves to apply a voltage between the working electrode 20A and the counter electrode 20B, measure a current, and control a potential of the working electrode 20A with reference to a potential of the reference electrode 20C. The control unit 21 detects endotoxin based on a current value measured by the potentiostat 21A and obtains an endotoxin content, records and totalizes test results, and displays the test results on a built-in display unit or outputs the test results to a device such as the hemodialyzer 6 that constitutes the dialysis system 1.

A washing water passage 22 that supplies reverse osmosis water as washing water from the reverse osmosis water supply device 2 is further connected to the drawing passage 16 between the on-off valve V1 and the pump P to provide supply means of the washing water. Also, a solution passage 24 that supplies a basic solution such as a sodium hydroxide solution or a potassium hydroxide solution from a solution container 23 is connected to the drawing passage 16 to provide supply means of the basic solution. An on-off valve V4 is provided in the washing water passage 22 and an on-off valve V5 is provided in the solution passage 24.

The basic solution acts to desorb endotoxin selectively adsorbed by the adsorbent 17, and also acts to hydrolyze the endotoxin and decompose a part of polysaccharide that constitutes the endotoxin into monosaccharide. In the present invention, the monosaccharides obtained by decomposition are detected by the electrochemical measurement so as to detect the endotoxin.

In the detection device 15 configured as described above, the control unit 21 controls actuation of the pump P and the on-off valves V1 to V5. An operation of the detection device 15 and a detection method of endotoxin will be described below.

The detection method using the detection device 15 of the present invention includes an adsorbing step of bringing the fluid to be tested into contact with the adsorbent 17 to cause the adsorbent 17 to adsorb endotoxin, a desorption step of bringing the basic solution into contact with the adsorbent 17 to desorb the adsorbed endotoxin, and a testing step of performing electrochemical measurement of the basic solution containing the desorbed endotoxin and detecting the endotoxin.

In the adsorbing step, from a state in which the pump P is stopped and the on-off valves V1 to V5 are closed, the on-off valves V1, V2 are opened and the pump P is actuated, and the fluid to be tested is drawn into the drawing passage 16 and passed through the column filled with the adsorbent 17. If the fluid to be tested is contaminated with endotoxin, the endotoxin is adsorbed by the adsorbent 17 while the fluid to be tested is in contact with the adsorbent 17. The fluid to be tested after contact with the adsorbent 17 is discharged through the opened on-off valve V2 to an outside of the device.

In the next desorption step, first, the on-off valve V1 is closed and the on-off valve V4 is opened, the reverse osmosis water is supplied as washing water to wash the adsorbent 17. In this way, substances other than the endotoxin adhering to the adsorbent 17 are washed away, so that only the endotoxin is adsorbed by the adsorbent 17. The substances washed away include protein or saccharides contained in the dialysate, and are prevented from being erroneously detected in the subsequent electrochemical measurement. The reverse osmosis water having passed through the adsorbent 17 is discharged through the opened on-off valve V2 to the outside of the device. If the fluid to be tested does not contain a substance that affects the measurement like the reverse osmosis water, this washing operation can be omitted.

Then, the on-off valve V4 is closed and the on-off valve V5 is opened to bring the basic solution into contact with the adsorbent 17, and the on-off valve V2 is closed and the on-off valve V3 is opened to introduce the basic solution into the inflow passage 18A in the measurement circuit 18. Thus, the endotoxin is desorbed from the adsorbent 17, and the basic solution containing the endotoxin flows through the flow path 19A in the measurement cell 19. The basic solution having passed through the measurement cell 19 flows out of the outflow passage 18B into the drawing passage 16 and is discharged to the outside of the device. In the desorption step, a part of polysaccharide of the endotoxin is decomposed into monosaccharide by hydrolysis action of the basic solution.

The testing step is performed in such a manner that the potentiostat 21A applies a voltage between the working electrode 20A and the counter electrode 20B while the basic solution passes through the measurement cell 19, and a current at that time is measured. The monosaccharide from the hydrolysis of the endotoxin in the basic solution oxidatively reacts on a surface of the working electrode 20A, thereby generating a current between the working electrode 20A and the counter electrode 20B. Since an amount of the current is proportional to a concentration of reacted monosaccharide, a current value can be measured to detect monosaccharide, and the endotoxin can be detected based on the amount of monosaccharide.

Figure 4:
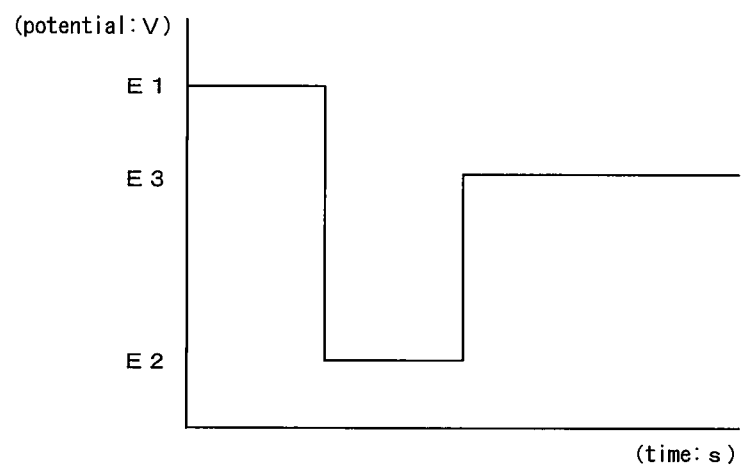
FIG. 4 shows a potential waveform of triple pulse amperometry (TPA)

However, the endotoxin includes polysaccharide and also a lipid portion, and the lipid portion tends to adsorb on the surface of working electrode 20A which would reduce both sensitivity and detection reproducibility. Thus, in the present invention, an electrochemical measurement method called triple pulse amperometry (TPA) is used to remove adsorbed lipid during the measurement and achieve high sensitivity and high reproducibility. Specifically, the triple pulse amperometry applies a cycle (one pulse) including three continuously changing different potentials and repeats the cycle a plurality of times to perform an electrochemical measurement. As shown in FIG. 4, a cycle is repeated in which switching from a measurement potential (E3) to a high potential (E1) causes adsorbed lipid, together with an oxidation product adhering to the working electrode 20A by an oxidation reaction in measurement, to be oxidized and peeled (cleaning), then switching to a potential (E2) lower than the measurement potential (E3) reduces the working electrode 20A (reactivation), and then the potential is switched to the measurement potential (E3). This can avoid accumulation of the oxidation product on the working electrode 20A, remove lipid adsorbed by the working electrode 20A to prevent a reduction in detection sensitivity, and always achieve detection of endotoxin with high sensitivity and high reproducibility.

Figure 5:
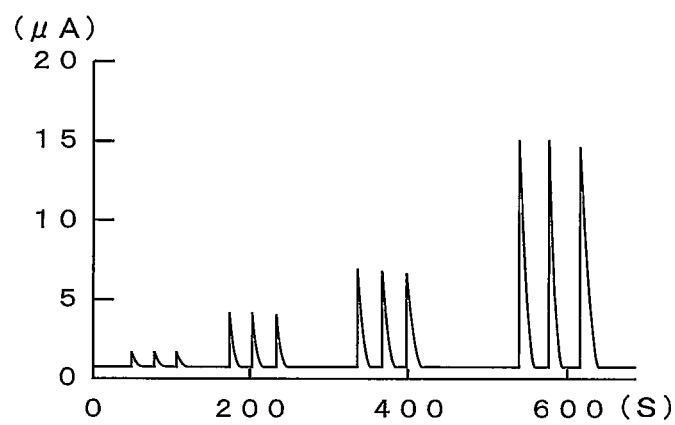
FIG. 5 is a graph of a current value showing a result of a detection experiment by a method for detecting endotoxin according to the present invention.

FIG. 5 shows a result of an endotoxin detection experiment using the detection device 15 according to the present invention, and shows a change in current value with time, the abscissa representing time and the ordinate representing the current value. In this experiment, one mole of potassium hydroxide solution is used as a basic solution, endotoxin is added to the potassium hydroxide solution, and electrochemical measurement is performed. The current value is measured by the triple pulse amperometry (TPA) while an amount of endotoxin per 1 ml of potassium hydroxide solution is increased from 1 µg to 5 µg, 10 µg, and 25 µg. Potentials of the triple pulse amperometry (TPA) are set to E1: +0.8 V, E2: −0.4 V, and E3: +0.3 V. It is apparent from the experiment result that the measured current value increases with increasing amount of endotoxin. It is supposed that a part of polysaccharide that constitutes the endotoxin is hydrolyzed with the basic solution into monosaccharide, and the monosaccharide exhibits electrochemical activity.

Figure 6:
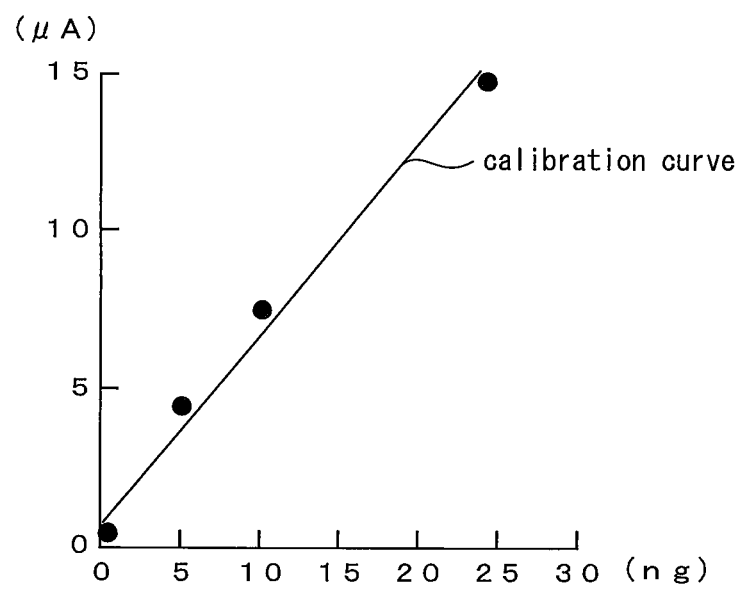
FIG. 6 shows a relationship between the current value and an amount of endotoxin based on the experiment result in FIG. 5.

FIG. 6 shows a relationship between the amount of endotoxin and the current value based on the experiment result in FIG. 5, and shows that the amount of endotoxin on the abscissa is substantially proportional to the current value on the ordinate. Specifically, FIG. 6 shows that sufficient reproducibility is achieved even if the monosaccharide exhibiting electrochemical activity is obtained by decomposing a part of polysaccharide of the endotoxin, and a calibration curve can be drawn for calculating the amount of endotoxin from the current value measured based on the monosaccharide.

In the above embodiment, the configuration in which the detection device 15 according to the present invention is connected to the dialysis system 1 and the hemodialyzer 6 has been described, but the detection device 15 may be provided alone. In this case, a sampled fluid to be tested is housed in a container such as a syringe or a bag, and introduced from the container into the drawing passage 16 with an opened front end.

What is claimed is:

1. A method for detecting endotoxin by electrochemical measurement, characterized by comprising the steps of:
   bringing a fluid to be tested into contact with an adsorbent that adsorbs endotoxin to adsorb the endotoxin;
   bringing a basic solution into contact with the adsorbent having adsorbed the endotoxin to desorb and hydrolyze the endotoxin from the adsorbent; and
   using triple pulse amperometry to electrochemically measure the basic solution containing the desorbed and hydrolyzed endotoxin.

2. The method for detecting endotoxin according to claim 1, characterized in that the fluid to be tested is a dialysate, and the adsorbent is washed with washing water before the basic solution is brought into contact with the adsorbent having adsorbed the endotoxin.

3. A device for detecting endotoxin by electrochemical measurement, characterized by comprising:
   an adsorbent that adsorbs endotoxin;
   supply means supplying a basic solution for desorbing the endotoxin; and
   measurement means specifically adapted for performing electrochemical measurement using triple pulse amperometry,
   wherein the device is configured to bring the fluid to be tested into contact with the adsorbent to adsorb the endotoxin, then bring the basic solution into contact with the adsorbent to desorb and hydrolyze the endotoxin, and the basic solution containing the desorbed and hydrolyzed endotoxin is electrochemically measured using triple pulse amperometry.

* * * * *